United States Patent [19]

DePriest

[11] Patent Number: 4,739,086

[45] Date of Patent: Apr. 19, 1988

[54] PRODUCTION OF ORGANIC VANADATES

[75] Inventor: Robert N. DePriest, Baton Rouge, La.

[73] Assignee: Ethyl Corporation, Richmond, Va.

[21] Appl. No.: 913,256

[22] Filed: Sep. 30, 1986

[51] Int. Cl.$^4$ .............................................. C07F 9/00
[52] U.S. Cl. ...................................................... 556/42
[58] Field of Search ......................................... 556/42

[56] References Cited

U.S. PATENT DOCUMENTS

| | | | |
|---|---|---|---|
| 2,220,041 | 11/1939 | Hill | 260/429 R |
| 3,652,617 | 3/1972 | Termin | 260/429 R |
| 3,657,295 | 4/1972 | McCoy | 260/429 R |
| 3,772,355 | 11/1973 | Merz | 260/429 R |
| 4,014,911 | 3/1977 | Muntz et al. | 260/429 R |
| 4,014,912 | 3/1977 | Muntz et al. | 260/429 R |

*Primary Examiner*—Paul F. Shaver
*Attorney, Agent, or Firm*—John F. Sieberth

[57] ABSTRACT

Vanadium oxytrihalide (e.g., $VOCl_3$) is reacted with alkali metal alkoxide (e.g., NaOEt) in the presence of a diluent (e.g., EtOH) that boils below the boiling point of the organic vanadate being produced. The diluent is then distilled from the reaction mixture and thereafter the organic vanadate is distilled from a suspension of the reaction products in an inert liquid hydrocarbon (e.g., mineral oil) that boils above the boiling point of the organic vanadate produced. This higher boiling hydrocarbon is preferably added to the reaction mixture after the diluent has been distilled off. The process avoids hydrogen halide evolution and consequent need for gaseous ammonia. Solvent extractions are not required, the process may be conducted in a single reactor, and the products are readily formed in high yields.

20 Claims, No Drawings

PRODUCTION OF ORGANIC VANADATES

FIELD

This invention relates to an improved process for the production of organic vanadates such as alkyl vanadates, cycloalkyl vanadates, aryl vanadates, and the like.

BACKGROUND

U.S. Pat. Nos. 4,014,911 and 4,014,912 describe the synthesis of triethylvanadate by reacting vanadium oxytrichloride with an alcohol in the presence of ammonia and a hydrocarbon solvent. In order to separate the by-product ammonium chloride, the product is extracted with an amide solvent (U.S. Pat. No. 4,014,911) or dimethyl sulfoxide (U.S. Pat. No. 4,014,912).

THE INVENTION

This invention provides a superior process for producing organic vanadates such as triethylvanadate and the like. By virtue of this invention:

Solvent extraction procedures which may introduce extraneous impurities and which in any event are time-consuming and tedious are rendered unnecessary.

Hydrogen halide evolution and the consequent need for gaseous ammonia are avoided.

The entire process can be conducted in a single reactor.

The desired products can be produced in high yields in conventional reaction equipment from inexpensive readily-available materials.

In accordance with this invention organic vanadates are produced by (i) reacting vanadium oxytrihalide with an alkali metal alkoxide in the presence of a diluent that boils at a temperature below the boiling point of the organic vanadate being produced, (ii) distilling the diluent from the reaction mixture, and (iii) distilling the organic vanadate from a suspension of the reaction products in an inert liquid hydrocarbon that boils at a temperature above the boiling point of the organic vanadate therein. Substitution of alkali metal cycloalkoxide or aryloxide for the alkali metal alkoxide in (i) yields the corresponding cycloalkyl and aryl vanadates.

Preferably the hydrocarbon is introduced into the reaction mixture after the diluent has been separated therefrom in accordance with (ii) above. However, all or a portion of the reaction of (i) above and the distillation of step (ii) above may be conducted in the presence of the higher boiling hydrocarbons of (iii).

In a preferred embodiment of this invention the diluent in (i) comprises an alkanol, most preferably the alkanol corresponding to the alkali metal alkoxide being used. By ensuring the presence of a suitable quantity of alkanol, the alkali metal alkoxide may be kept in solution during the reaction. In short, use of an alkanol as the diluent offers the opportunity of conducting the reaction of (i) in solution. Other diluents that may be used include liquid hydrocarbons and ethers having boiling points below the boiling point of the organic vanadate being produced. Except for alcohols, the diluents used in the process should be inert. Suitable inert diluents of this type include pentane, hexane, heptane, octane, nonane, decane, 2,2,4-trimethylpentane, benzene, toluene, xylene, cyclopentane, cyclohexane, cyclooctane, 1,2,3,4-tetrahydronaphthalene, low boiling petroleum ethers, 1,2-dimethoxyethane, tetrahydrofuran, diglyme, and the like, as well as mixtures of such materials.

As noted above, the entire operation described may be conducted in a single reactor, if desired.

In order to isolate pure organic vanadates recourse may be had to further purification for example, by subjecting the product to additional distillation.

It will be understood of course that the operations described above should be conducted under a relatively inert atmosphere such as under a blanket of an inert gas (nitrogen, argon, helium or the like). Likewise, it is desirable to ensure that the materials used are substantially anhydrous.

The process of this invention is applicable to the synthesis of any organic vanadate which is distillable either under atmospheric or reduced pressure conditions. Illustrative vanadates which may be produced include trimethylvanadate, tripropylvanadate, triisopropylvanadate, tributylvanadate, tri-2-ethylhexylvanadate, tridecylvanadate, triphenylvanadate, tritolylvanadate, trixylylvanadate, tricyclopentylvanadate, tricyclohexylvanadate, tribenzylvanadate, tricyclopropylcarbinylvanadate, tri-2-methoxyethylvanadate, and the like.

In conducting the process it is advantageous to form the alkali metal alkoxide in situ and to employ an excess of the alcohol (or phenol) used relative to the amount of alkali metal employed in forming the alkali metal alkoxide (or aryl oxide). The excess alcohol (or phenol) serves as a diluent and, as noted above, offers the possibility of conducting the reaction of (i) in the liquid phase. Of the alkali metals, use of sodium is preferred because of its ready availability and low cost. However, use may be made of potassium or the other alkali metals should this be desired. By the same token, alkaline earth metals such as calcium and magnesium may be used in forming the alkoxides or aryloxides for use in the reaction. Other metal alkoxides that may be employed include zinc alkoxides, aluminum alkoxides, titanium alkoxides, zirconium alkoxides, and the like.

When forming the alkali metal alkoxide in situ it is desirable to add the alkali metal in incremental portions with vigorous stirring or agitation.

Vanadium oxytrichloride is the preferred vanadium reactant for use in the process. However, use may be made of the other vanadium oxytrihalides such as vanadium oxytribromide, vanadium oxytrifluoride, and the like. The reaction between the alkoxide and the vanadium oxytrihalide should be conducted at a temperature below the boiling point of the vanadium oxytrihalide and the diluent being used. In most cases, temperatures falling within the range of about $-10°$ to about $125°$ C. and preferably from about $10°$ to about $75°$ C. will be used. However, departures from these temperature ranges are deemed feasible and may be used. Atmospheric or superatmospheric pressures may be used as desired.

Any of a wide variety of hydrocarbons may be used in step (iii) above, provided, of course, that the boiling point of the hydrocarbon(s) employed is higher than the boiling point of the organic vanadate being produced. Mineral oil and other liquid high boiling paraffinic, aromatic or naphthenic hydrocarbons may be employed for this purpose.

The practice and advantages of this invention will become still further apparent from the following illustrative example.

EXAMPLE

A solution of sodium ethoxide (NaOEt) in excess ethanol (EtOH) was prepared by adding 12 g of sodium (freshly cut into small pieces under petroleum ether) to a 500 mL flask containing 75 g of anhydrous EtOH. The sodium was added in increments over a period of 120 minutes and was accompanied by vigorous stirring of the flask contents. A nitrogen atmosphere was maintained in the flask.

In a dry box, 26.9 g (0.155 mole) of vanadium oxychloride was charged to a dropping funnel along with 30 mL of dry petroleum ether.

The NaOEt/EtOH mixture was cooled to 0° C. and the $VOCl_3$ was added to the chilled mixture by means of the dropping funnel over a 20-minute period. A light yellowish suspension of finely divided solids was formed. The reaction mixture was stirred for 30 minutes at room temperature and 50 mL of petroleum ether was added. After several attempts to remove the solids by filtration failed because of frit pluggage, 50 mL of dry mineral oil was added to the reaction mixture and the EtOH and petroleum ether were stripped off over a period of 1.5 hours using pressures of 100 down to 25 mm Hg and an external water bath held at 30° to 40° C. The remaining contents of the flask were subjected to a flash distillation by raising the temperature of the bath from 40° to 105° C. while reducing the pressure to 0.2 mm of Hg over a 45-minute period. This yielded 42 g of a clear light yellow liquid. $^1H$ NMR showed the mixture to contain 70.4 wt. % of triethylvanadate (VO(OEt)$_3$) and 29.6 wt. % of EtOH. The yield of triethyl vanadate was 94%. Subsequent fractional distillation gave 23.3 g of clear yellow triethylvanadate (bp 84°–85° C. at 3.2±0.2 mm Hg.

Similar procedures may be used for preparing other organic vanadates in accordance with this invention.

As is well known, organic vanadates are useful for a number of applications including components for olefin polymerization catalyst systems and as dopants for use in the manufacture of semiconductor devices.

This invention is susceptible to considerable variation within the spirit and scope of the appended claims.

What is claimed is:

1. A process for the production of organic vanadates which comprises (i) reacting vanadium oxytrihalide with alkali metal alkoxide in the presence of a diluent that boils below the boiling point of the organic vanadate being produced, (ii) distilling the diluent from the reaction mixture and (iii) distilling the organic vanadate from a suspension of the reaction products in an inert liquid hydrocarbon that boils above the boiling point of the organic vanadate present therein.

2. A process in accordance with claim 1 wherein said liquid hydrocarbon is introduced into the reaction products after the diluent has been distilled therefrom in accordance with (ii).

3. A process in accordance with claim 1 wherein the organic vanadate recovered in accordance with (iii) is subjected to further purification by distillation.

4. A process in accordance with claim 1 wherein the vanadium oxytrihalide is vanadium oxytrichloride.

5. A process in accordance with claim 1 wherein the alkali metal alkoxide is a sodium alkoxide.

6. A process in accordance with claim 1 wherein the vanadium oxytrihalide is vanadium oxytrichloride and the alkali metal alkoxide is a sodium alkoxide.

7. A process for the production of organic vanadates which comprises (i) reacting vanadium oxytrihalide with a mixture of alkali metal alkoxide and alkanol, (ii) distilling excess alkanol from the reaction mixture, and (iii) distilling the organic vanadate from a suspension of the reaction products in an inert liquid hydrocarbon that boils above the boiling point of the organic vanadate.

8. A process in accordance with claim 7 wherein said liquid hydrocarbon is introduced to the reaction products after excess alkanol has been distilled therefrom in accordance with (ii).

9. A process in accordance with claim 7 wherein the organic vanadate recovered in accordance with (iii) is subjected to further purification by distillation.

10. A process in accordance with claim 7 wherein in the metal alkoxide is a sodium alkoxide.

11. A process in accordance with claim 7 wherein the vanadium oxytrihalide is vanadium oxytrichloride and the alkali metal alkoxide is a sodium alkoxide.

12. A process in accordance with claim 7 wherein the quantity of alkanol in (i) is sufficient to keep at least a substantial portion of the alkali metal alkoxide in solution.

13. A process in accordance with claim 7 wherein the quantity of alkanol in (i) is sufficient to keep at least a substantial portion of the alkali metal alkoxide in solution, and wherein said liquid hydrocarbon is introduced into the reaction products after the alkanol has been distilled therefrom in accordance with (ii).

14. A process in accordance with claim 7 wherein the alkali metal alkoxide is formed in situ by reaction of the alkali metal with excess alkanol.

15. A process for the production of triethylvanadate which comprises (i) reacting vanadium oxytrichloride with a mixture of sodium ethoxide and ethanol, (ii) separating excess ethanol from the reaction mixture by distillation, and (iii) distilling triethyl vanadate from a suspension of the reaction products in an inert hydrocarbon that boils above the boiling point of triethylvanadate.

16. A process in accordance with claim 15 wherein said hydrocarbon is introduced into the reaction products after excess ethanol has been distilled therefrom in accordance with (ii).

17. A process in accordance with claim 15 wherein the quantity of ethanol in (i) is sufficient to keep at least a substantial portion of the sodium ethoxide in solution.

18. A process in accordance with claim 15 wherein the triethylvanadate recovered in accordance with (iii) is subjected to further purification by distillation.

19. A process in accordance with claim 15 wherein the sodium ethoxide is formed in situ by incrementally adding sodium to excess ethanol.

20. A process in accordance with claim 15 wherein the sodium ethoxide is formed in situ by incrementally adding sodium to excess ethanol, wherein the quantity of ethanol in (i) is sufficient to keep at least a substantial portion of the sodium ethoxide in solution, and wherein said hydrocarbon is introduced into the reaction products after excess ethanol has been distilled therefrom in accordance with (ii).

* * * * *